US010888702B2

(12) United States Patent
Stahmann et al.

(10) Patent No.: US 10,888,702 B2
(45) Date of Patent: Jan. 12, 2021

(54) PROGRESSIVE ADAPTIVE DATA TRANSFER

(71) Applicant: Cardiac Pacemakers, Inc., St. Paul, MN (US)

(72) Inventors: Jeffrey E. Stahmann, Ramsey, MN (US); Howard D. Simms, Jr., Shoreview, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 122 days.

(21) Appl. No.: 15/400,950

(22) Filed: Jan. 6, 2017

(65) Prior Publication Data

US 2017/0199970 A1    Jul. 13, 2017

Related U.S. Application Data

(60) Provisional application No. 62/276,662, filed on Jan. 8, 2016.

(51) Int. Cl.
*A61N 1/372* (2006.01)
*G06F 19/00* (2018.01)
*G16H 50/20* (2018.01)

(52) U.S. Cl.
CPC ..... *A61N 1/37252* (2013.01); *G06F 19/3418* (2013.01); *G16H 50/20* (2018.01)

(58) Field of Classification Search
CPC .... A61N 1/3627; G06F 19/00; G06F 19/3418
See application file for complete search history.

(56) References Cited

U.S. PATENT DOCUMENTS 4,172,459 A    10/1979    Hepp
4,552,154 A    11/1985    Hartlaub
(Continued)

FOREIGN PATENT DOCUMENTS

WO    WO9965393 A1    12/1999
WO    2009114755 A2    9/2009
WO    2011034468 A1    3/2011

OTHER PUBLICATIONS

International Search Report and Written Opinion issued in PCT/US2017/012641, dated Apr. 24, 2017, 14 pages.
(Continued)

*Primary Examiner* — Reginald R Reyes
(74) *Attorney, Agent, or Firm* — Faegre Drinker Biddle & Reath LLP

(57) ABSTRACT

An interrogation system for a medical device includes a memory storing a diagnostic algorithm, a processor configured to run the diagnostic algorithm, and a communication module configured to facilitate data transfer between the interrogation system and the medical device. The diagnostic algorithm is configured to reach a diagnostic conclusion based on data from the medical device. The diagnostic algorithm is configured to iteratively interrogate the medical device for the data from the medical device until the diagnostic algorithm reaches the diagnostic conclusion, each iterative interrogation requesting additional data as compared to prior iterations. The communication module is configured to receive the additional data from the medical device in response to each iterative interrogation. The diagnostic algorithm is further configured to store an indication of the diagnostic conclusion within the memory.

14 Claims, 5 Drawing Sheets

(56) References Cited

U.S. PATENT DOCUMENTS

| | | | |
|---|---|---|---|
| 5,127,404 | A | 7/1992 | Wyborny et al. |
| 5,251,621 | A | 10/1993 | Collins |
| 5,800,466 | A | 9/1998 | Routh et al. |
| 5,833,623 | A | 11/1998 | Mann et al. |
| 5,902,250 | A | 5/1999 | Verrier et al. |
| 5,904,708 | A | 5/1999 | Goedeke |
| 6,073,049 | A | 6/2000 | Alt et al. |
| 6,076,015 | A | 6/2000 | Hartley et al. |
| 6,132,384 | A | 10/2000 | Christopherson et al. |
| 6,190,324 | B1 | 2/2001 | Kieval et al. |
| 6,490,479 | B2 | 12/2002 | Bock |
| 6,804,558 | B2 | 10/2004 | Haller et al. |
| 6,890,306 | B2 | 5/2005 | Poezevera |
| 6,978,182 | B2 | 12/2005 | Mazar et al. |
| 7,146,206 | B2 | 12/2006 | Glass et al. |
| 7,395,117 | B2 | 7/2008 | Mazar et al. |
| 7,559,903 | B2 | 7/2009 | Moussavi et al. |
| 7,751,876 | B2 | 7/2010 | Healey |
| 7,787,946 | B2 | 8/2010 | Stahmann et al. |
| 7,996,074 | B2 | 8/2011 | Kenknight et al. |
| 8,002,553 | B2 | 8/2011 | Hatlestad et al. |
| 8,049,489 | B2 | 11/2011 | Gauglitz et al. |
| 8,108,048 | B2 | 1/2012 | Masoud |
| 8,126,548 | B2 | 2/2012 | Ding et al. |
| 8,145,590 | B2 | 3/2012 | Brockway et al. |
| 8,209,011 | B2 | 6/2012 | Freeberg |
| 8,396,543 | B2 | 3/2013 | Hoeppner et al. |
| 8,423,142 | B2 | 4/2013 | Freeberg |
| 8,611,000 | B2 | 12/2013 | Komatsu et al. |
| 8,639,318 | B2 | 1/2014 | Hatlestad et al. |
| 8,694,116 | B2 | 4/2014 | Kenknight et al. |
| 8,731,661 | B2 | 5/2014 | White |
| 8,791,815 | B2 | 7/2014 | Mazar et al. |
| 8,849,682 | B2 | 9/2014 | Mahajan et al. |
| 8,915,741 | B2 | 12/2014 | Hatlestad et al. |
| 8,929,981 | B2 | 1/2015 | Perschbacher et al. |
| 8,983,603 | B2 | 3/2015 | Perschbacher et al. |
| 9,014,807 | B2 | 4/2015 | Bocek et al. |
| 9,020,602 | B2 | 4/2015 | Aghassian |
| 9,037,240 | B2 | 5/2015 | Gunderson |
| 9,610,025 | B2 | 4/2017 | Zhang |
| 2001/0051787 | A1* | 12/2001 | Haller ................. G06F 8/65 604/66 |
| 2002/0072783 | A1 | 6/2002 | Goedeke et al. |
| 2003/0028080 | A1 | 2/2003 | Lebel et al. |
| 2005/0042589 | A1 | 2/2005 | Hatlestad et al. |
| 2005/0251227 | A1 | 11/2005 | Khoo et al. |
| 2005/0288599 | A1 | 12/2005 | MacAdam et al. |
| 2006/0241708 | A1 | 10/2006 | Boute |
| 2007/0255330 | A1 | 11/2007 | Lee et al. |
| 2007/0286469 | A1* | 12/2007 | Yamagata ............ G06T 7/0012 382/131 |
| 2008/0183245 | A1 | 7/2008 | van Oort et al. |
| 2009/0058635 | A1 | 3/2009 | LaLonde et al. |
| 2009/0063187 | A1 | 3/2009 | Johnson et al. |
| 2009/0088821 | A1 | 4/2009 | Abrahamson |
| 2010/0057167 | A1 | 3/2010 | Evers et al. |
| 2010/0152815 | A1 | 6/2010 | Vandanacker |
| 2010/0185251 | A1 | 7/2010 | Propato |
| 2010/0241182 | A1 | 9/2010 | Whitman et al. |
| 2010/0280841 | A1 | 11/2010 | Dong et al. |
| 2011/0046698 | A1 | 2/2011 | Kivi et al. |
| 2011/0270109 | A1 | 11/2011 | Zhang et al. |
| 2012/0029373 | A1 | 2/2012 | Stadler et al. |
| 2012/0078131 | A1 | 3/2012 | Zong |
| 2012/0154152 | A1 | 6/2012 | Rantala et al. |
| 2012/0165887 | A1 | 6/2012 | Lee et al. |
| 2012/0188096 | A1 | 7/2012 | Corndorf et al. |
| 2012/0232416 | A1 | 9/2012 | Gilham et al. |
| 2012/0253207 | A1* | 10/2012 | Sarkar ................. A61B 5/7275 600/483 |
| 2012/0283544 | A1 | 11/2012 | Kraetschmer et al. |
| 2012/0296228 | A1 | 11/2012 | Zhang et al. |
| 2013/0144178 | A1 | 6/2013 | Halperin et al. |
| 2013/0237773 | A1 | 9/2013 | An et al. |
| 2013/0274624 | A1 | 10/2013 | Mahajan et al. |
| 2014/0277243 | A1 | 9/2014 | Maskara et al. |
| 2015/0216433 | A1 | 8/2015 | Thakur et al. |
| 2015/0282738 | A1 | 10/2015 | Thakur et al. |
| 2015/0342487 | A1 | 12/2015 | Thakur et al. |
| 2016/0045125 | A1 | 2/2016 | Krueger et al. |
| 2018/0220373 | A1* | 8/2018 | Arzelier ............ H04W 52/0241 |

OTHER PUBLICATIONS

International Search Report and Written Opinion issued in PCT/US2017/012649, dated Mar. 29, 2017, 18 pages.

International Search Report and Written Opinion issued in PCT/US2017/012651, dated Mar. 24, 2017, 12 pages.

International Search Report and Written Opinion issued in PCT/US2017/020831, dated Jun. 16, 2017, 11 pages.

Passman, Rod S., et al. "Development and Validation of a Dual Sensing Scheme to Improve Accuracy of Bradycardia and Pause Detection in an Insertable Cardiac Monitor." Heart Rhythm, 14:1016-1023, 2017.

Sarkar, Shantanu, et al. "A Dual Sensing Scheme to Reduce Inappropriate Detection of Bradycardia and Pauses in an Insertable Cardiac Monitor." 2016 Heart Rhythm, 15 pages.

International Preliminary Report on Patentability issued in PCT/US2017/020831, dated Sep. 13, 2018, 7 pages.

\* cited by examiner

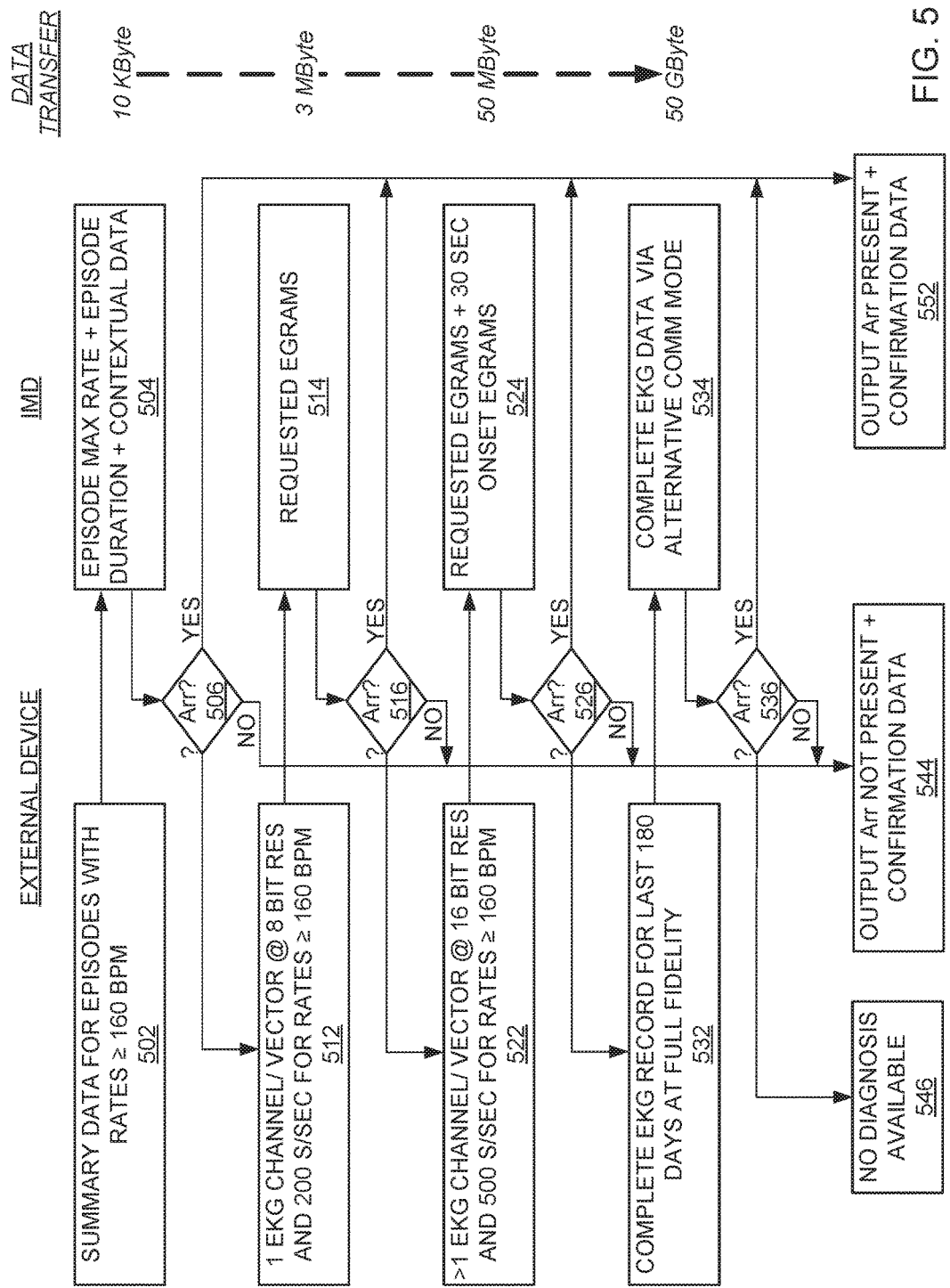

PROGRESSIVE ADAPTIVE DATA TRANSFER

CROSS-REFERENCE TO RELATED APPLICATION

This application claims priority to Provisional Application No. 62/276,662, filed Jan. 8, 2016, which is herein incorporated by reference in its entirety.

TECHNICAL FIELD

The present disclosure relates to data transfer techniques in a medical device system.

BACKGROUND

Medical devices including therapy delivery and/or physiological sensing elements are often configured to communicate with devices external to themselves. These medical devices may include implantable medical devices (IMDs), wearable medical devices (WMDs), otherwise portable medical devices, and/or the like. Implantable stimulation devices are one example of IMDs that may be configured to communicate with external devices. Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc.

Medical devices may be configured to communicate with an external device such as, for example, another medical device (e.g., an IMD, WMD, etc.), an external controller (e.g., a portable interrogation device, hand-held programmer, clinician's programmer, etc.), an external communications device (e.g., a repeater, router, etc.), and/or the like. For example, an external controller may be used to wirelessly send data to, and receive data from, an IMD. Additionally, an external controller may send programming data to control therapy and/or sensing functions of an IMD. Also, an external controller may receive data from the IMD, such as therapy history, diagnostic information and/or physiological sensing information.

Various data transfer techniques may be used to facilitate communications between medical devices and external devices. Such techniques include wireless data telemetry, which may take place via radio frequency (RF) communications, such as Bluetooth or Medical Implant Communication Service (MICS) protocols or through inductive coupling, such as magnetic inductive coupling. Alternatively, or additionally, wired techniques can be used. One such technique uses a data transfer mode utilizing conducted electrical energy though tissue as part of, or the entire, transfer path between two or more devices. The wired transfer mode may use one or more electrodes adhesively connected to skin.

SUMMARY

Semiconductor technology is rapidly increasing the amount of data medical devices can store. However, in comparison with rapidly increasing data storage capacity, data transfer technology and battery technology is not developing at equivalent rates. Thus, the energy required to transfer data is not decreasing as quickly as the memory is increasing. The disclosed techniques facilitate utilizing higher data storage capacities while limiting volumes of data transferred to external devices by medical devices.

In an Example 1, an interrogation system for a medical device comprises: a memory storing a diagnostic algorithm; a processor configured to run the diagnostic algorithm; and a communication module configured to facilitate data transfer between the interrogating system and the medical device, wherein the diagnostic algorithm is configured to reach a diagnostic conclusion based on data from the medical device, wherein the diagnostic algorithm is configured to iteratively interrogate the medical device for the data from the medical device until the diagnostic algorithm reaches the diagnostic conclusion, each iterative interrogation requesting additional data as compared to prior iterations, wherein the communication module is configured to receive the additional data from the medical device in response to each iterative interrogation, and wherein the diagnostic algorithm is further configured to store an indication of the diagnostic conclusion within the memory.

In an Example 2, the interrogation system of Example 1, wherein the processor is configured to select a communication technique for the data transfer between the interrogation system and the medical device according to at least one of a volume of the data in the data transfer, a time available for the data transfer, and an energy available for the data transfer.

In an Example 3, the interrogation system of Example 2, wherein the selected communication technique includes one or more of: radio frequency communications; inductive communications; and externally powered communications.

In an Example 4, the interrogation system of any one of Examples 1-3, wherein the diagnostic algorithm is configured to detect a cardiac arrhythmia.

In an Example 5, the interrogation system of any one of Examples 1-4, wherein the additional data includes an additional data type as compared to prior iterations.

In an Example 6, the interrogation system of any one of Examples 1-5, wherein the additional data includes data representing additional events as compared to prior iterations.

In an Example 7, the interrogation system of any one of Examples 1-6, wherein the additional data includes one or more of: a higher data sample rate as compared to prior iterations; a higher data sample resolution as compared to prior iterations; a longer data sample length as compared to prior iterations; and a lower data sample threshold as compared to prior iterations.

In an Example 8, the interrogation system of any one of Examples 1-7, wherein the memory, the processor and the communication module are part of a clinician programmer.

In an Example 9, a medical system comprises: the interrogation system of any one of Examples 1-8; and the medical device, wherein the medical device comprises a housing encasing control electronics, a medical device communication module, and a medical device memory, wherein the control electronics are configured to store diagnostic data within the medical device memory and provide requested portions of the diagnostic data to the interrogation system via the medical device communication module in response to the iterative interrogations from the communication module of the interrogation system.

In an Example 10, the medical system of Example 9, wherein the medical device includes one or more of: an electrical stimulation device; a drug delivery device; and a physiological sensor.

In an Example 11, a method comprising: interrogating, via a communication module, a medical device for diagnostic data; receiving, via the communication module, a portion of diagnostic data obtained by the medical device; analyzing, via a diagnostic algorithm configured to determine a diagnostic conclusion, the portion of diagnostic data; iteratively interrogating the medical device for additional diagnostic data and, for each iteration, analyzing, via the diagnostic algorithm, the additional diagnostic data until reaching the diagnostic conclusion based on the diagnostic data; and storing an indication of the diagnostic conclusion within a memory.

In an Example 12, the method of Example 11, further comprising selecting a communication technique for the data transfer with the medical device according to at least one of a volume of the data in the data transfer, a time available for the data transfer, and an energy available for the data transfer.

In an Example 13, the method of Example 11 or Example 12, wherein the diagnostic conclusion includes detection of a presence of a cardiac arrhythmia.

In an Example 14, the method of any one of Examples 11-13, wherein the additional data includes one or more of: an additional data type as compared to prior iterations; data representing additional events as compared to prior iterations; a higher data sample rate as compared to prior iterations; a higher data sample resolution as compared to prior iterations; a longer data sample length as compared to prior iterations; and a lower data sample threshold as compared to prior iterations.

In an Example 15, the method of any one of Examples 11-14, wherein the medical device includes one or more of: an electrical stimulation device; a drug delivery device; and a physiological sensor.

In an Example 16, an interrogation system for a medical device comprising: a memory storing a diagnostic algorithm; a processor configured to run the diagnostic algorithm; and a communication module configured to facilitate data transfer between the interrogation system and the medical device, wherein the diagnostic algorithm is configured to reach a diagnostic conclusion based on data from the medical device, wherein the diagnostic algorithm is configured to iteratively interrogate the medical device for the data from the medical device until the diagnostic algorithm reaches the diagnostic conclusion, each iterative interrogation requesting additional data as compared to prior iterations, wherein the communication module is configured to receive the additional data from the medical device in response to each iterative interrogation, and wherein the diagnostic algorithm is further configured to store an indication of the diagnostic conclusion within the memory.

In an Example 17, the interrogation system of Example 16, wherein the processor is configured to select a communication technique for the data transfer between the interrogation system and the medical device according to at least one of a volume of the data in the data transfer, a time available for the data transfer, and an energy available for the data transfer.

In an Example 18, the interrogation system of Example 17, wherein the selected communication technique includes one or more of radio frequency communications; inductive communications; and externally powered communications.

In an Example 19, the interrogation system of Example 16, wherein the diagnostic algorithm is configured to detect a cardiac arrhythmia.

In an Example 20, the interrogation system of Example 16, wherein the additional data includes an additional data type as compared to prior iterations.

In an Example 21, the interrogation system of Example 16, wherein the additional data includes data representing additional events as compared to prior iterations.

In an Example 22, the interrogation system of Example 16, wherein the additional data includes one or more of: a higher data sample rate as compared to prior iterations; a higher data sample resolution as compared to prior iterations; a longer data sample length as compared to prior iterations; and a lower data sample threshold as compared to prior iterations.

In an Example 23, the interrogation system of Example 16, wherein the memory, the processor and the communication module are part of a clinician programmer.

In an Example 24, a medical system comprises: a medical device comprising a housing encasing control electronics, a medical device communication module, and a medical device memory, wherein the control electronics are configured to store diagnostic data within the memory; and an interrogation system for a medical device comprising: a memory storing a diagnostic algorithm; a processor configured to run the diagnostic algorithm; and a communication module configured to facilitate data transfer between the interrogation system and the medical device, wherein the diagnostic algorithm is configured to iteratively interrogate the medical device for the data from the medical device until the diagnostic algorithm reaches a diagnostic conclusion, each iterative interrogation requesting additional data as compared to prior iterations, wherein the control electronics are configured to provide requested portions of the diagnostic data to the interrogation system via the medical device communication module in response to the iterative interrogations from the communication module of the interrogation system, wherein the communication module is configured to receive the additional data from the medical device in response to each iterative interrogation, wherein the diagnostic algorithm is configured to reach the diagnostic conclusion based on data from the medical device, and wherein the diagnostic algorithm is further configured to store an indication of the diagnostic conclusion within the memory.

In an Example 25, the medical system of Example 24, wherein the processor is configured to select a communication technique for the data transfer between the interrogation system and the medical device according to at least one of a volume of the data in the data transfer, a time available for the data transfer, and an energy available for the data transfer.

In an Example 26, the medical system of Example 25, wherein the selected communication technique includes one or more of: radio frequency communications; inductive communications; and externally powered communications.

In an Example 27, the medical system of Example 24, wherein the diagnostic algorithm is configured to detect a cardiac arrhythmia.

In an Example 28, the medical system of Example 24, wherein the additional data includes one or more of: an additional data type as compared to prior iterations; data representing additional events as compared to prior iterations; a higher data sample rate as compared to prior iterations; a higher data sample resolution as compared to prior iterations; a longer data sample length as compared to prior iterations; and a lower data sample threshold as compared to prior iterations.

In an Example 29, the medical system of Example 24, wherein the memory, the processor and the communication module are part of a clinician programmer.

In an Example 30, the medical system of Example 24, wherein the medical device includes one or more of: an electrical stimulation device; a drug delivery device; and a physiological sensor.

In an Example 31, a method comprises: interrogating, via a communication module, a medical device for diagnostic data; receiving, via the communication module, a portion of diagnostic data stored in a memory of the medical device; analyzing, via a diagnostic algorithm, the portion of diagnostic data; upon determining the portion of diagnostic data is insufficient to reach a diagnostic conclusion according to the diagnostic algorithm, iteratively interrogating the medical device for additional diagnostic data and, for each iteration, analyzing, via the diagnostic algorithm, the additional diagnostic data until reaching the diagnostic conclusion based on the diagnostic data; and storing an indication of the diagnostic conclusion within a memory.

In an Example 32, the method of Example 31, further comprising selecting a communication technique for the data transfer with the medical device according to at least one of a volume of the data in the data transfer, a time available for the data transfer, and an energy available for the data transfer.

In an Example 33, the method of Example 31, wherein the diagnostic conclusion includes detection of a presence of a cardiac arrhythmia.

In an Example 34, the method of Example 31, wherein the additional data includes one or more of: an additional data type as compared to prior iterations; data representing additional events as compared to prior iterations; a higher data sample rate as compared to prior iterations; a higher data sample resolution as compared to prior iterations; a longer data sample length as compared to prior iterations; and a lower data sample threshold as compared to prior iterations.

In an Example 35, the method of Example 31, wherein the medical device includes one or more of: an electrical stimulation device; a drug delivery device; and a physiological sensor.

While multiple examples are disclosed, still other examples of the present this disclosure will become apparent to those skilled in the art from the following detailed description, which shows and describes illustrative examples of this disclosure. Accordingly, the drawings and detailed description are to be regarded as illustrative in nature and not restrictive.

BRIEF DESCRIPTION OF THE DRAWINGS

FIG. 5 is a flowchart illustrating an example diagnostic algorithm configured to iteratively interrogate an IMD to determine the presence or absence of an arrhythmia.

Figure 1:
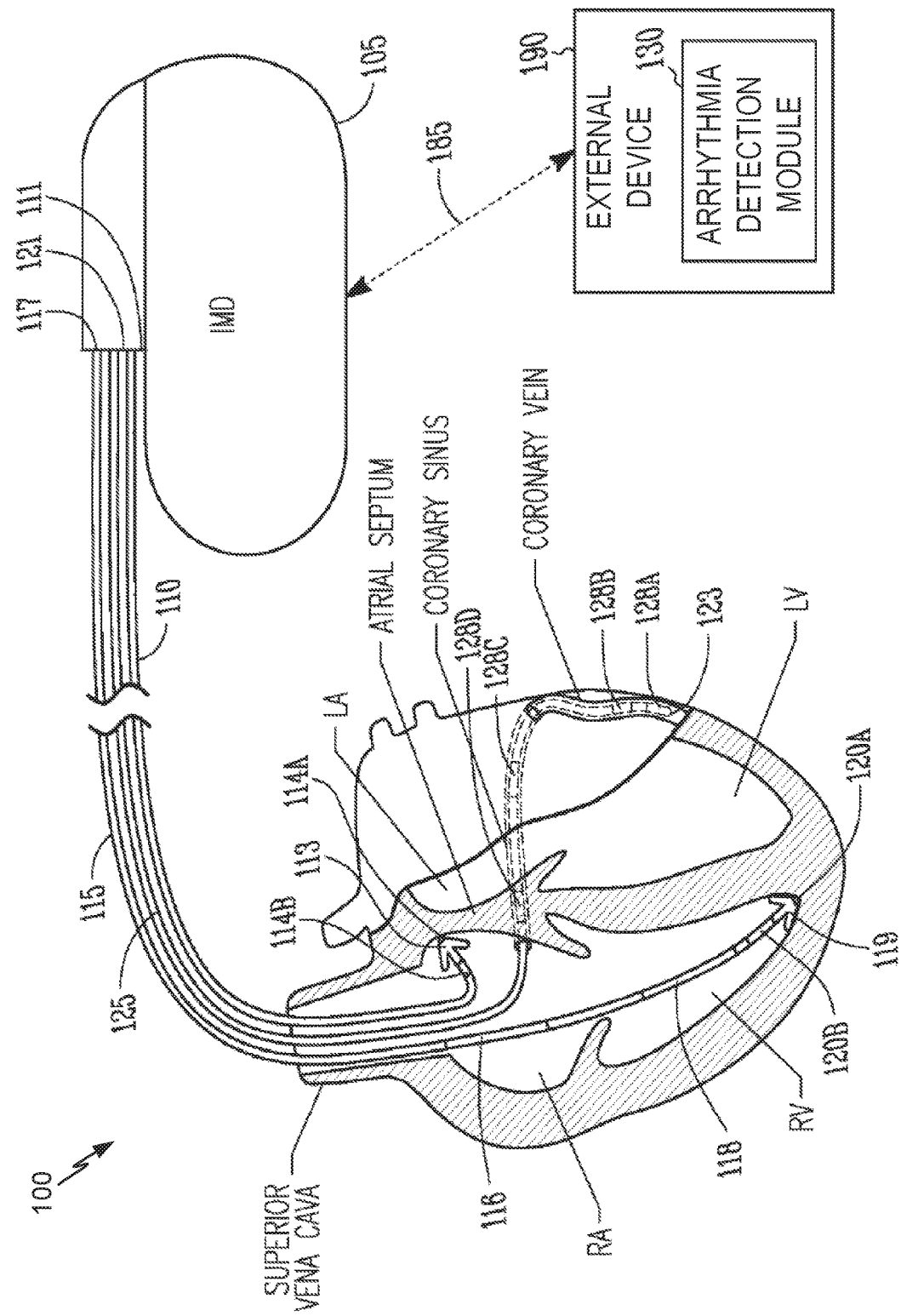
FIG. 1 shows a medical system including an IMD and an external device with a wireless data connection to the IMD.

While this disclosure is amenable to various modifications and alternative forms, specific examples have been shown by way of example in the drawings and are described in detail below. The intention, however, is not to limit this disclosure to the particular examples described. On the contrary, this disclosure is intended to cover all modifications, equivalents, and alternatives falling within the scope of this disclosure as defined by the appended claims.

DETAILED DESCRIPTION

FIG. 1 shows a medical system 100, including an IMD 105 and an external device 190, with a wireless data connection, telemetry link 185, between IMD 105 and external device 190. In this example of FIG. 1, medical system 100 is a cardiac rhythm management (CRM) system 100. IMD 105 is electrically coupled to a heart through implantable leads 110, 115, and 125. External device 190 communicates with IMD 105 via telemetry link 185.

IMD 105 includes a hermetically sealed can housing control electronics including an electronic circuit that senses physiological signals and delivers therapeutic electrical pulses. The hermetically sealed can may also function as a can electrode for sensing and/or pulse delivery purposes. IMD 105 may sense one or more cardiac signals, including signals indicative of one or more arrhythmia episodes, and may generate cardiac data representative of the one or more cardiac signals. For example, the control electronics of IMD 105 may sense and store one or more cardiac signals on a continuous basis as facilitated by the higher data storage capacities provided by the rapid improvements in semiconductor technologies. Additionally or alternatively, IMD 105 may store one or more cardiac signals on an episodic basis. In one example, IMD 105 includes a pacemaker that delivers cardiac pacing therapies. In another example, IMD 105 includes a pacemaker and a cardioverter/defibrillator that delivers cardioversion/defibrillation therapies. In various examples, IMD 105 includes one or more devices selected from monitoring devices and therapeutic devices such as a pacemaker, a cardioverter/defibrillator, a neurostimulator, a drug delivery device, and a biological therapy device. In one example, the pacemaker provides for cardiac resynchronization therapy (CRT).

Lead 110 is a right atrial (RA) pacing lead that includes an elongate lead body having a proximal end 111 and a distal end 113. Proximal end 111 is coupled to a connector for connecting to IMD 105. Distal end 113 is configured for placement in the RA in or near the atrial septum. Lead 110 includes an RA tip electrode 114A, and an RA ring electrode 114B. RA electrodes 114A and 114B are incorporated into the lead body at distal end 113 for placement in or near the atrial septum, and are each electrically coupled to IMD 105 through a conductor extending within the lead body. RA tip electrode 114A, RA ring electrode 114B, and/or the can electrode allow for sensing an RA electrogram indicative of RA depolarizations and delivering RA pacing pulses.

Lead 115 is a right ventricular (RV) pacing-defibrillation lead that includes an elongate lead body having a proximal end 117 and a distal end 119. Proximal end 117 is coupled to a connector for connecting to IMD 105. Distal end 119 is configured for placement in the RV. Lead 115 includes a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava (SVC). Defibrillation electrode 118 is incorporated into the lead body near distal end 119 for placement in the RV. RV electrodes 120A and 120B are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or the can electrode allow for delivery of cardioversion/defibrillation pulses to the heart. RV tip electrode 120A, RV ring electrode 120B, and/or the can of IMD 105 allow for sensing an RV electrogram indicative of RV depolarizations and delivering RV pacing pulses. In various examples, proximal defibrillation electrode 116 and/or distal defibrillation electrode 118 may also be used for sensing the RV electrogram.

Lead 125 is a left ventricular (LV) coronary pacing lead that includes an elongate lead body having a proximal end 121 and a distal end 123. Proximal end 121 is coupled to a connector for connecting to IMD 105. Distal end 123 is configured for placement in the coronary vein. Lead 125 includes an LV tip electrode 128A, a distal LV ring electrode 128B, and two proximal LV ring electrodes 128C and 128D. The distal portion of lead 125 is configured for placement in the coronary sinus and coronary vein such that LV electrodes 128A and 128B are placed in the coronary vein, and LV electrodes 128C and 128D are placed in or near the coronary sinus. LV electrodes 128A and 128B are incorporated into the lead body at distal end 123 and are each electrically coupled to IMD 105 through a conductor extending within the lead body. LV tip electrode 128A, distal LV ring electrode 128B, proximal LV ring electrode 128C, proximal LV ring electrode 128D, and/or the can electrode allow for sensing an LV electrogram indicative of LV depolarizations and delivering LV pacing pulses.

Electrodes from different leads may also be used to sense an electrogram or deliver pacing or cardioversion/defibrillation pulses. For example, an electrogram may be sensed using an electrode selected from RV electrode 116, 118, and 120A-B and another electrode selected from LV electrode 128A-D. The lead configuration including RA lead 110, RV lead 115, and LV lead 125 is illustrated in FIG. 1 by way of example and not by way of restriction. Other lead configurations may be used, depending on monitoring and therapeutic requirements. For example, additional leads may be used to provide access to additional cardiac regions, and leads 110, 115, and 125 may each include more or fewer electrodes along the lead body at, near, and/or distant from the distal end, depending on specified monitoring and therapeutic needs.

In some examples, a wireless sensing and/or therapy system may be used in which, for example, IMD 105 communicates with one or more other implanted devices to facilitate sensing and/or delivering therapy. For example, in embodiments, IMD 105 may be configured to communicate with, and control, one or more leadless pacing seeds implanted in or near the heart. In various examples, IMD 105 senses the one or more cardiac signals using any combination of electrodes, such as those illustrated in FIG. 1, suitable for detection and classification of the one or more arrhythmia episodes.

External device 190 may include a programmer and/or other components of a patient monitoring system such as, for example, a repeater, a cellular phone, a computing device, and/or the like. External device 190 may include an external therapy and/or sensing device such as, for example, a wearable defibrillator, an external cardiac monitor, and/or the like. External device 190 allows for programming of IMD 105 as well as diagnostic analysis of physiological sensor data and may receive data from IMD 105 representative of signals acquired by IMD 105 via telemetry link 185.

Telemetry link 185 provides for data transmission from IMD 105 to external device 190. Data transmission from IMD 105 to external device 190 may include, for example, physiological data acquired by and stored in IMD 105, therapy history data stored in IMD 105, and data indicating an operational status of IMD 105 (e.g., battery status and lead impedance). The physiological data include the cardiac data representative of the one or more cardiac signals.

Telemetry link 185 also provides for data transmission from external device 190 to IMD 105. This may include, for example, programming IMD 105 to acquire physiological data, programming IMD 105 to perform at least one self-diagnostic test (such as for a device operational status), programming IMD 105 to run a signal analysis algorithm (such as an algorithm implementing tachyarrhythmia detection) and programming IMD 105 to deliver pacing and/or cardioversion/defibrillation therapies.

Telemetry link 185 may include an inductive telemetry link, a far-field radio-frequency telemetry link, another data transfer link or a combination of multiple data transfer links. Telemetry link 185 occurs transcutaneously, i.e., through the patient's tissue, making it particularly useful in a medical implantable device system. For an inductive telemetry link close proximity and proper orientation between the antennas for IMD 105 and external device 190 and 13 will generally improve the coupling between them, but deviation from ideal orientations can still result in suitably reliable data transfer. In any event, as compared to RF wireless communication techniques, and inductive telemetry link may provide lower power consumption for a given volume of data, but may also be more inconvenient for a patient as the external device is secured in close proximity with the internal device during the data transfer. As discussed in further detail with respect to FIG. 5, the data transfer link may vary according to a quantity of data to be transferred between IMD 105 and external device 190.

The term "telemetry link" may refer to an ability to communicate some type of information in at least one direction between at least two devices, and should not be understood to be limited to a direct, persistent, or otherwise limited communication channel. That is, according to some examples, the telemetry link 185 may be a persistent communication link, an intermittent communication link, an ad-hoc communication link, and/or the like. The telemetry link 185 may refer to direct communications between IMD 105 and external device 190, and/or indirect communications that travel between IMD 105 and external device 190 via at least one other device (e.g., a repeater, router, hub, cell phone and/or the like). The telemetry link 185 may facilitate uni-directional and/or bi-directional communication between the IMD 105 and external device 190.

External device 190 includes an arrhythmia detection module 130 that detects the presence of arrhythmias based on cardiac data acquired by and telemetered from IMD 105. Arrhythmia detection module 130 further includes non-transitory computer-readable memory for storing diagnostic data received from an IMD, such as the continuous or episodic cardiac signals from IMD 105. In various examples, arrhythmia detection module 130 may iteratively interrogate IMD 105 for diagnostic data until the arrhythmia detection module 130 reaches a diagnostic conclusion, e.g., the presence or absence of an arrhythmia.

The circuit of CRM system 100 may be implemented using a combination of hardware, software, and/or firmware.

In various examples, each element of IMD 105 and external device 190, including its various examples, may be implemented using an application-specific circuit constructed to perform one or more particular functions or a general-purpose circuit programmed to perform such function(s). Such a general-purpose circuit includes, but is not limited to, a microprocessor or portions thereof, a microcontroller or portions thereof, and a programmable logic circuit or portions thereof. For example, arrhythmia detection module 130 may include a set of computer-executable instructions stored in a memory that, when executed by a processor, causes the processor to perform aspects of embodiments of the functionality of the arrhythmia detection module 130 described herein.

In embodiments, the memory includes computer-readable media in the form of volatile and/or nonvolatile memory and may be removable, nonremovable, or a combination thereof. The memory may include non-transitory computer-readable media. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. The computer-executable instructions may include, for example, computer code, machine-useable instructions, and the like such as, for example, program components capable of being executed by one or more processors. Program components may be programmed using any number of different programming environments, including various languages, development kits, frameworks, and/or the like.

Figure 2:
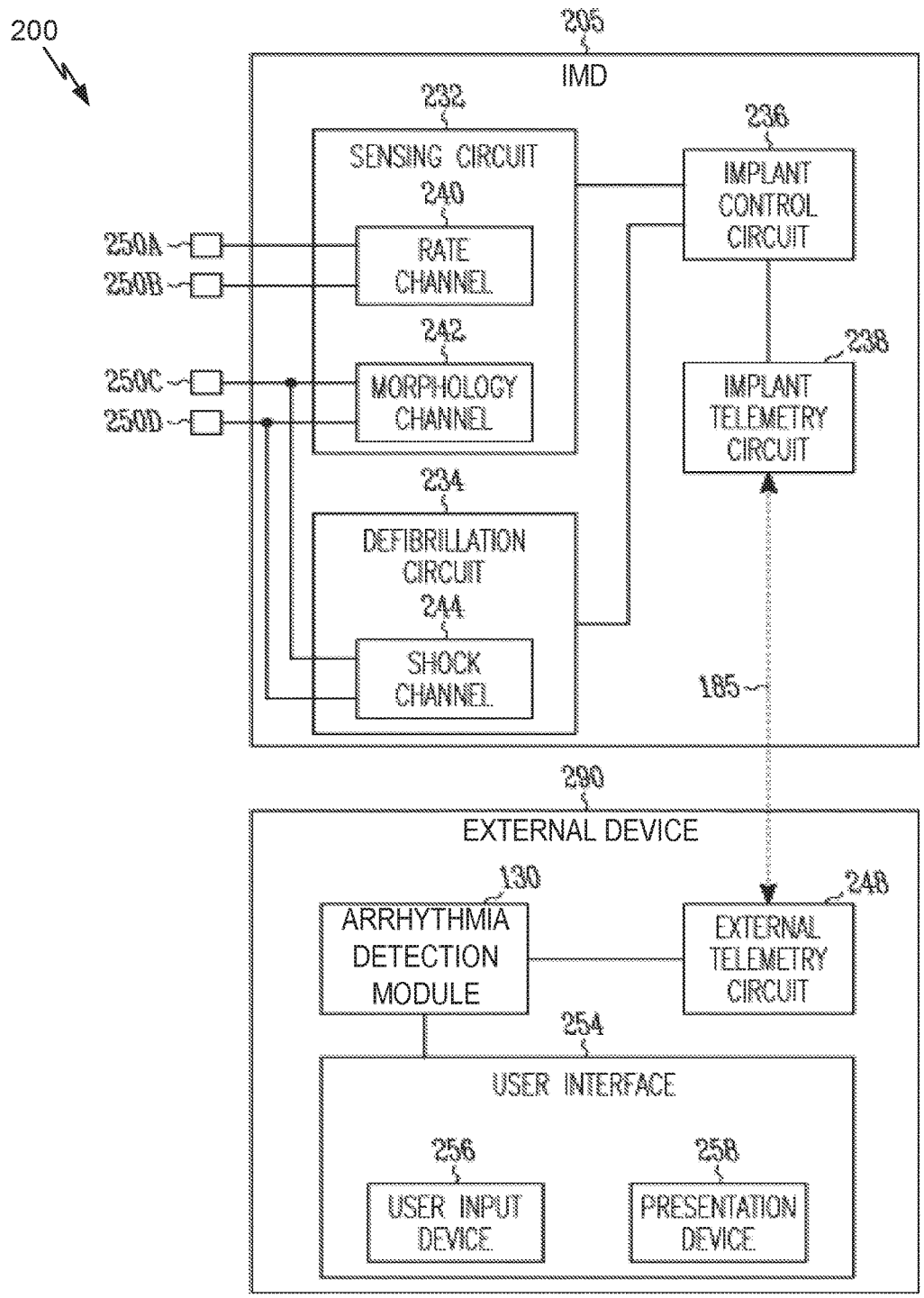
FIG. 2 is a block diagram illustrating data transfer between an IMD and an external device.

FIG. 2 is a block diagram illustrating an example of portions of a circuit of IMD 205 and portions of a circuit of an external device 290 of a medical system 200. IMD 205 represents an example of IMD 105 and includes a sensing circuit 232, a defibrillation circuit 234, control electronics including an implant control circuit 236, and an IMD communication module 238. In one example, IMD 205 is an implantable cardioverter defibrillator (ICD). Sensing circuit 232 includes a rate channel 240 and a morphology channel 242. Rate channel 240 senses a regional cardiac signal through electrodes 250A and 250B for use in heart beat detection. Morphology channel 242 senses a global cardiac signal through electrodes 250C and 250D for use in morphological analysis.

In some examples, rate channel 240 senses a regional ventricular electrogram through an RV tip electrode such as electrode 120A and an RV coil electrode such as electrode 118, and morphology channel 242 senses a global ventricular electrogram through the RV coil electrode and an SVC coil electrode such as electrode 116. In this example, electrode 250A is the RV tip electrode, electrodes 250B and 250C are the same RV coil electrode, and electrode 250D is the SVC coil electrode. In the same or different examples, the SVC coil electrode is electrically connected to the can electrode.

Defibrillation circuit 234 includes a shock channel 244 to deliver cardioversion/defibrillation pulses (shocks). In the illustrated example, shock channel 244 delivers the shocks using the same pair of electrodes as used by morphology channel 242 (so the "morphology channel" is also referred to as the "shock channel"). In an alternative example, a single cardiac signal is sensed for use in heart rate detection and morphology analysis, such as through electrodes 250C and 250D. While this alternative example eliminates the need for sensing two cardiac signals, the example as illustrated in FIG. 2 provides for more robust heart beat detection. Implant control circuit 236 controls the operation of IMD 205 including the sensing of the one or more cardiac signals and the delivery of the shocks. Implant control circuit 236 also includes the physical IMD memory, a non-transitory computer-readable memory, for storing the one or more continuous or episodic cardiac signals. IMD communication module 238 supports the functions of telemetry link 185, including transmitting the cardiac data from IMD 205 to external device 290.

External device 290 represents an example of external device 190 and may represent a hand-held programmer or a clinician's programmer. External device 190 includes arrhythmia detection module 130, an external telemetry circuit 248, and a user interface 254. Implant telemetry circuit 248 supports the functions of telemetry link 185, including receiving the cardiac data transmitted from IMD 205. User interface 254 includes a user input device 256 and a presentation device 258. User input device 256 receives various commands and parameters from the user for controlling operations of IMD 205 and external device 290. Presentation device 258 presents various patient and device information including the detection and diagnostic conclusion information generated by arrhythmia detection module 130. User interface 254 may be similar to that used for a computer, cell phone, or other hand held electronic device, and may include touchable buttons and a display for example, allowing a user, such as a clinician, to operate the external device 290.

Arrhythmia detection module 130 includes a diagnostic algorithm configured to analyze data received from IMD 205 to reach a diagnostic conclusion, such as the presence or absence of an arrhythmia within a patient associated with IMD 205. In various examples, arrhythmia detection module 130 may iteratively interrogate IMD 205 via external telemetry circuit 248, an example of a wireless communication module, for diagnostic data until the arrhythmia detection module 130 reaches the diagnostic conclusion. In other examples, a different wired or wireless communication module may be used for iteratively interrogation. Each iterative interrogation may request additional data as compared to prior iterations until reaching the diagnostic conclusion. In response to the requests, IMD 205 is configured to provide requested portions of the diagnostic data to arrhythmia detection module 130 via the implant telemetry circuit 238, an example of an IMD communication module. Arrhythmia detection module 130 may further store an indication of the diagnostic conclusion within its non-transitory computer-readable memory and/or present an indication of the diagnostic conclusion to a user via user interface 254.

Figure 3:
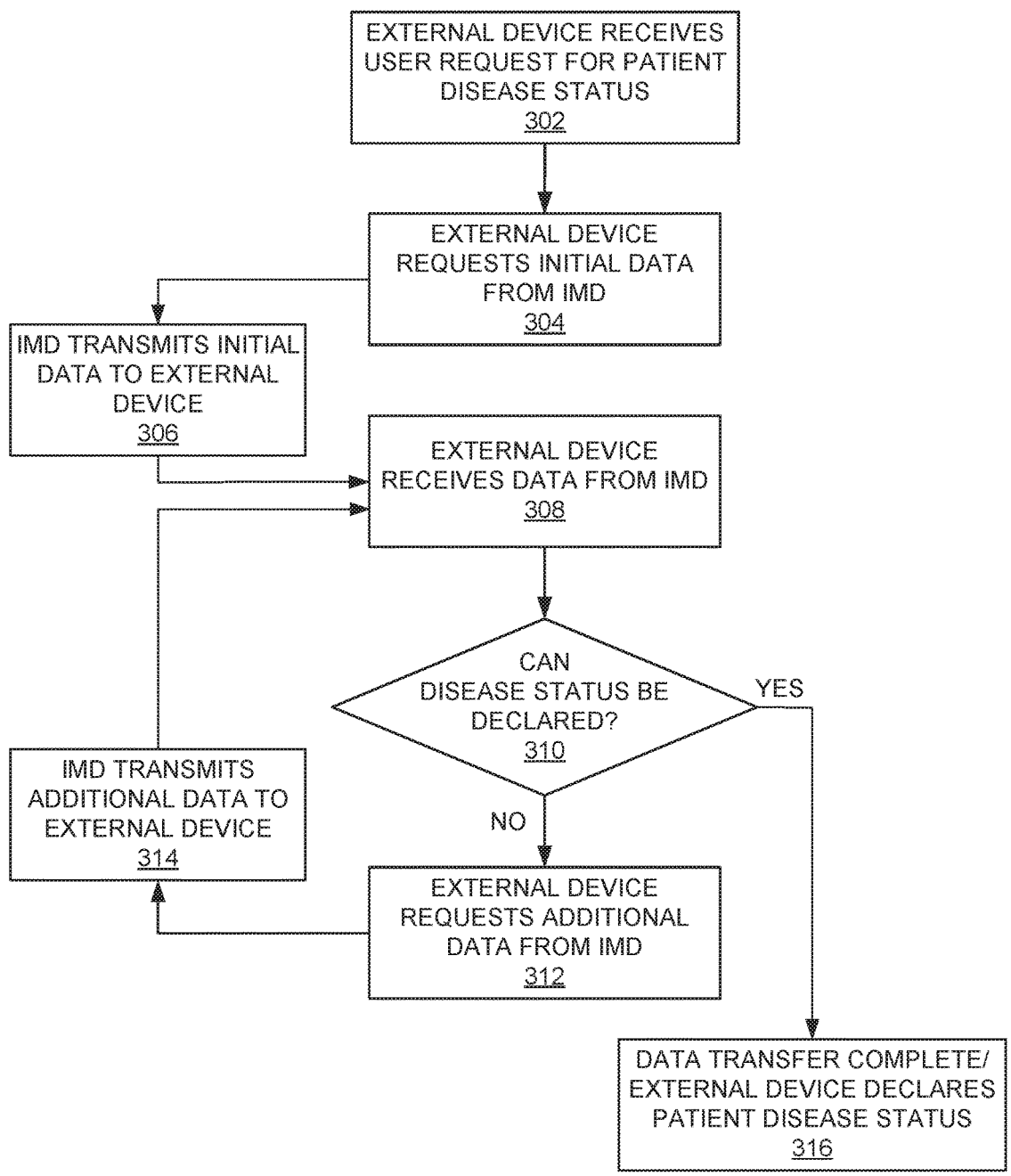
FIG. 3 is a flowchart illustrating example techniques for a diagnostic algorithm configured to iteratively interrogate an IMD for data until the diagnostic algorithm reaches a diagnostic conclusion.

FIG. 3 is a flowchart illustrating example techniques for a diagnostic algorithm configured to iteratively interrogate an IMD for data until the diagnostic algorithm reaches a diagnostic conclusion. The techniques of FIG. 3 may be implemented as part of an IMD system, including, but not limited to the IMD systems described with respect to FIGS. 1 and 2. However, the techniques of FIG. 3 are not limited to cardiac sensing and stimulation systems, but may be applied to any variety of medical systems that are configured to transfer data between a first component of the medical system, such as sensing device or device storing diagnostic information, and a second component of the medical system, the second component including a diagnostic module that analyzes received diagnostic data. In various examples, the techniques of FIG. 3 could be readily applied to cardiac stimulation and/or sensing systems, neurostimulation and/or sensing systems, drug delivery systems, such as those including infusion pumps, medical systems including other electrical stimulation, sonic stimulation, chemical delivery or other therapeutic functions, medical systems including other electrical, pressure or other physiological sensing functions or other medical systems. In this manner, the techniques of this disclosure should not be considered limited to the particular example medical systems described herein as they may be readily adapted to any variety of medical systems. For clarity, the techniques of FIG. 3 are described with respect to medical system 200 of FIG. 2.

By way of example, external device 290 optionally receives a user request for a patient disease status for a patient associated with IMD 205 (302). For example, the disease status may represent detection of atrial fibrillation, as described in the example of FIG. 4, detection of cardiac arrhythmia, as described in the example of FIG. 5, support monitoring of pulmonary/abdominal/peripheral edema, disordered breathing, patient posture, patient activity or other patient information sensed by IMD 205. As discussed above with respect to FIG. 2, external device 290 communicates with IMD 205 via a wireless communication link between external telemetry circuit 248, an example of a wireless communication module, of external device 290 and implant telemetry circuit 238 of IMD 205. External device 290 interrogates IMD 205 for diagnostic data (304). In response to the request, IMD 205 transmits an initial set of diagnostic data to external device 290, the initial set of diagnostic data representing only a portion of the diagnostic data stored in the memory of IMD 205 (306). External device 290 receives the initial set of diagnostic data from IMD 205 (308), and analyzes, via a diagnostic algorithm, such as arrhythmia detection module 130, the initial set of diagnostic data (310).

In the event that the initial set of diagnostic data is sufficient to declare a disease state, external device 290 declares the diagnostic conclusion, a patient disease status in this example, and stores the diagnostic conclusion within a memory of external device 290 or another device (316). Following the diagnostic conclusion, external device 290 may also present an indication of the diagnostic conclusion to a user via user interface 254.

Upon determining the initial set of diagnostic data is insufficient to reach a diagnostic conclusion according to the diagnostic algorithm, external device 290 requests additional data from IMD 205 (312). In various examples, the additional data may represent an additional data type as compared to prior iterations, data representing additional events as compared to prior iterations, a higher data sample rate as compared to prior iterations, a higher data sample resolution as compared to prior iterations, a longer data sample length as compared to prior iterations, a lower data sample threshold as compared to prior iterations and/or other additional data. In response to the request, IMD 205 transmits additional diagnostic data to external device 290 (314). External device 290 receives the additional diagnostic data from IMD 205 (308), and analyzes, via a diagnostic algorithm, such as arrhythmia detection module 130 the additional data in combination with the initial set of diagnostic data to evaluate whether the combined data is sufficient to reach a diagnostic conclusion (310).

In the event the combined diagnostic data is insufficient to reach a diagnostic conclusion according to the diagnostic algorithm, external device 290 may again request additional data from IMD 205 (312). This process repeats until the diagnostic algorithm running on external device 290 has enough information to reach a diagnostic conclusion or until the entirety of the relevant diagnostic data stored in memory of IMD 205 is transferred to external device 290. In this manner, external device 290 iteratively interrogates IMD 205 for additional diagnostic data and, for each iteration, analyzes, via the diagnostic algorithm, the additional diagnostic data until reaching the diagnostic conclusion based on the diagnostic data. Once the diagnostic data is sufficient to declare a disease state, external device 290 declares the diagnostic conclusion and stores the diagnostic conclusion within a non-transitory computer-readable memory of external device 290 or another device (316). Following the diagnostic conclusion, external device 290 may also present an indication of the diagnostic conclusion to a user via user interface 254.

Figure 4:
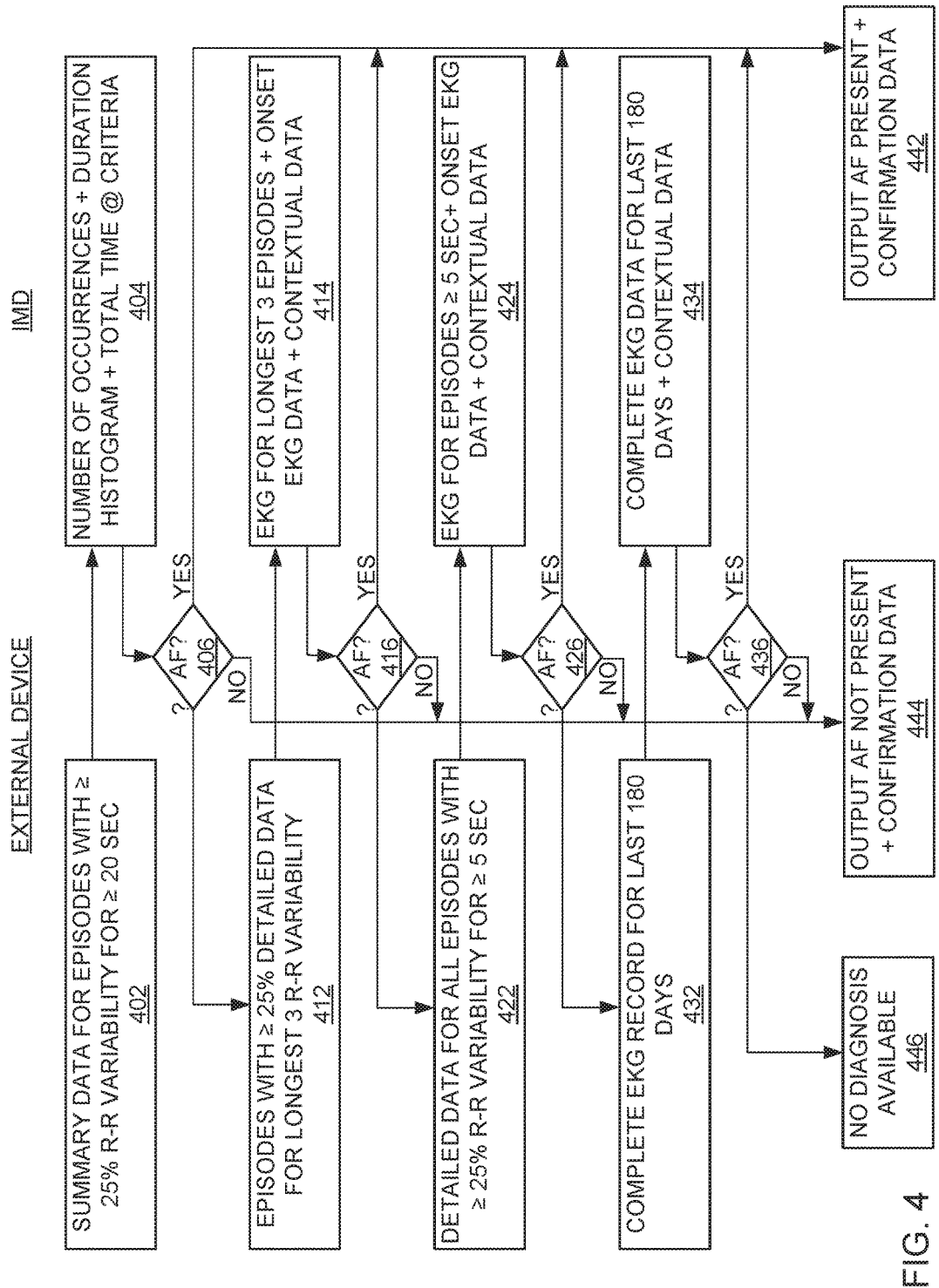
FIG. 4 is a flowchart illustrating an example diagnostic algorithm configured to iteratively interrogate an IMD to determine the presence or absence of atrial fibrillation.

FIG. 4 illustrates a more specific example of a diagnostic algorithm configured to iteratively interrogate an IMD for data until the diagnostic algorithm reaches a diagnostic conclusion. In particular, FIG. 4 illustrates example techniques for detection of atrial fibrillation. In the example of FIG. 4, for each iterative interrogation, the additional data represents an additional data type. The techniques of FIG. 4 may be implemented as part of a medical system including cardiac sensing that might be indicative of atrial fibrillation. Such medical systems include, but are not limited to, the IMD systems described with respect to FIGS. 1 and 2. For clarity, the techniques of FIG. 4 are described with respect to medical system 200 of FIG. 2.

As discussed with respect to FIG. 3, external device 290 optionally receives a user request for a patient disease status, in this example the presence or absence of atrial fibrillation, for a patient associated with IMD 205. As discussed above with respect to FIG. 2, external device 290 communicates with IMD 205 via a wireless communication link between external telemetry circuit 248, an example of a wireless communication module, of external device 290 and implant telemetry circuit 238 of IMD 205. External device 290 interrogates IMD 205 for an initial set of diagnostic data, summary data of cardiac episodes including at least twenty-five percent R-R variability for at least twenty seconds, where R is a point corresponding to the peak of the QRS complex of the electrocardiogram (EKG) wave of a cardiac signal of the patient's heart (402). In response to the request, IMD 205 transmits an initial set of diagnostic data to external device 290, the initial set of diagnostic data including a number of occurrences of cardiac episodes including at least twenty-five percent R-R variability for at least twenty seconds, a duration histogram, and the total time of the cardiac episodes including at least twenty-five percent R-R variability (404). Such information represents only a limited portion of the diagnostic data stored in the memory of IMD 205. For example, the volume of data within this initial set of diagnostic data may range between 1 and 100 kilobytes, such that data transfer between IMD 205 and external device 290 under any variety of wireless connections is fast and requires limited power consumption. External device 290 receives the initial set of diagnostic data from IMD 205, and analyzes, via a diagnostic algorithm, such as arrhythmia detection module 130, the initial set of diagnostic data to determine the presence or absence of atrial fibrillation (406). According to some examples, the analysis of the initial set of diagnostic data may produce one of three outcomes: a determination of the presence of atrial fibrillation, a determination of the absence of atrial fibrillation or a determination that the initial set of diagnostic data is insufficient to reach a diagnostic conclusion according to the diagnostic algorithm.

In the event that the diagnostic data is sufficient to declare a disease state, external device 290 declares the diagnostic conclusion, i.e., either the presence or absence of atrial fibrillation and stores the diagnostic conclusion within a memory of external device 290 or another device. External device 290 may further output the determination of the presence of atrial fibrillation as well as confirmation data supporting the same (442) or output the determination of the absence of atrial fibrillation as well as confirmation data supporting the same (444). The output of the diagnostic conclusion may include storing such information in a memory and/or presenting an indication of the diagnostic conclusion to a user via a user interface.

Alternatively, upon determining the initial set of diagnostic data is insufficient to reach a diagnostic conclusion of the presence or absence of atrial fibrillation according to the diagnostic algorithm, external device 290 requests additional data from IMD 205. In this example, the additional data represents an additional data type as compared to the initial iteration, detailed data for the three longest cardiac episodes with at least twenty-five percent R-R variability (412). In response to the request, IMD 205 transmits an additional set of diagnostic data to external device 290, the additional set of diagnostic data including the requested data and optionally including onset EKG data as well as contextual data associated with the three cardiac episodes (414). Such contextual data may include by way of example, but is not limited to, dates, times of day, postures, respiration rates, and/or patient activity levels coincident with the three longest cardiac episodes. The volume of data within this iteration of diagnostic data may range between 1 and 10 megabytes, such that data transfer between IMD 205 and external device 290 under any variety of wireless connections is still practical, although more time and power is required than with the initial data transfer of step 404.

External device 290 receives the additional diagnostic data from IMD 205, and analyzes, via a diagnostic algorithm, such as arrhythmia detection module 130, the additional diagnostic data in combination with the initial set of diagnostic data to determine the presence or absence of atrial fibrillation (416). In the event that diagnostic data is sufficient to declare a disease state, external device 290 declares the diagnostic conclusion as discussed above with respect to the initial iteration. In the event the combined diagnostic data is insufficient to reach a diagnostic conclusion according to the diagnostic algorithm, external device 290 may again request additional data from IMD 205. In this example, the additional data represents an additional data type as compared to the prior iterations, detailed data for all cardiac episodes with at least twenty-five percent R-R variability of at least five seconds (422). In response to the request, IMD 205 transmits an additional set of diagnostic data to external device 290, the additional set of diagnostic data including the requested data and optionally including onset EKG data as well as contextual data associated with the three cardiac episodes (424). The volume of data within this iteration of diagnostic data may range between 10 and 100 megabytes, such that data transfer between IMD 205 and external device 290 under any variety of wireless connections may still be practical, although more time and power is required than with prior iterations.

External device 290 receives the additional diagnostic data from IMD 205, and analyzes, via a diagnostic algorithm, such as arrhythmia detection module 130, the additional diagnostic data in combination with the diagnostic data of the prior iterations to determine the presence or absence of atrial fibrillation (426). In the event that the diagnostic data is sufficient to declare a disease state, external device 290 declares the diagnostic conclusion as discussed above with respect to the initial iteration. In the event the combined diagnostic data is insufficient to reach a diagnostic conclusion according to the diagnostic algorithm, external device 290 may again request additional data from IMD 205. In this example, the additional data represents an additional data type as compared to the prior iterations, a complete EKG record recorded by IMD 105, such as data recorded over the last 180 days (432). The storage of a continuous history of sensor data, such as an EKG, within a memory of IMD 205 is facilitated by the higher data storage capacities provided by the rapid improvements in semiconductor technologies.

In response to the request, IMD 205 transmits an additional set of diagnostic data to external device 290, the additional set of diagnostic data including the requested data and optionally including onset EKG data as well as contextual data associated with the three cardiac episodes (434). The volume of data within this iteration of diagnostic data may range between 1 and 100 gigabytes, such that data transfer between IMD 205 and external device 290 under some wireless connections may be impractical. For this reason, a higher speed or lower power wireless connection between IMD 205 and external device 290 may be used than with prior iterations. Examples of relatively suitable wireless connections for large volumes of data include inductive telemetry and externally powered communications like RFID. In some examples, external device 290 may notify a user via user interface 254 that an antenna of external device needs to be positioned in closer proximity to IMD 205 or an antenna of IMD 205 to facilitate the data transfer. In such examples, external device 290 and IMD 205 may communicate via a more convenient wireless connection, such as a RF connection, for example a Bluetooth or MICS connection, in prior iterations before switching to lower power, but less convenient, communication technique for the data transfer iteration of step 434.

External device 290 receives the additional diagnostic data from IMD 205, and analyzes, via a diagnostic algorithm, such as arrhythmia detection module 130, the additional diagnostic data in combination with the diagnostic data of the prior iterations to determine the presence or absence of atrial fibrillation (436). In the event that the diagnostic data is sufficient to declare a disease state, external device 290 declares the diagnostic conclusion as discussed above with respect to the initial iteration. In the event the combined diagnostic data is insufficient to reach a diagnostic conclusion according to the diagnostic algorithm, external device 290 declares the diagnostic data is insufficient to reach a diagnostic conclusion (446). External device 290 may store an indication that the diagnostic data is insufficient to reach a diagnostic conclusion within a memory of external device 290 or another device and/or present an indication that the diagnostic data is insufficient to reach a diagnostic conclusion to a user via user interface 254.

FIG. 5 illustrates another specific example of a diagnostic algorithm configured to iteratively interrogate an IMD for data until the diagnostic algorithm reaches a diagnostic conclusion. In particular, FIG. 5 illustrates example techniques for detection of a cardiac arrhythmia. In the example of FIG. 5, for each iterative integration, the additional data represents additional cardiac events as compared to prior iterations. The techniques of FIG. 5 may be implemented as part of a medical system including cardiac sensing that might be indicative of a cardiac arrhythmia. Such medical systems include, but are not limited to, the IMD systems described with respect to FIGS. 1 and 2. For clarity, the techniques of FIG. 5 are described with respect to medical system 200 of FIG. 2.

As discussed with respect to FIG. 3, external device 290 optionally receives a user request for a patient disease status, in this example the presence or absence of a cardiac arrhythmia, for a patient associated with IMD 205. External device 290 interrogates IMD 205 for an initial set of diagnostic data, summary data of cardiac episodes including heartrates of at least 160 beats per minute (BPM) (502). In response to the request, IMD 205 transmits an initial set of diagnostic data to external device 290, the initial set of diagnostic data including the maximum heart rate for each requested episode, the duration of each requested episode, and, optionally, contextual data associated with each requested episode (504). Such contextual data may include by way of example, but is not limited to, dates, times of day, postures, respiration rates, and/or patient activity levels coincident with the cardiac episodes. The diagnostic information in this initial iteration represents only a limited portion of the diagnostic data stored in the memory of IMD 205. For example, the volume of data within this initial set of diagnostic data may range between 1 and 100 kilobytes, such as approximately 10 kilobytes, such that data transfer between IMD 205 and external device 290 under any variety of wireless connections is fast and requires limited power consumption.

External device 290 receives the initial set of diagnostic data from IMD 205, and analyzes, via a diagnostic algorithm, such as arrhythmia detection module 130, the initial set of diagnostic data to determine the presence or absence of a cardiac arrhythmia (506). According to some examples, the analysis of the initial set of diagnostic data may produce one of three outcomes: a determination of the presence of a cardiac arrhythmia, a determination of the absence of a cardiac arrhythmia or a determination that the initial set of diagnostic data is insufficient to reach a diagnostic conclusion according to the diagnostic algorithm.

In the event that the diagnostic data is sufficient to declare a disease state, external device 290 declares the diagnostic conclusion, i.e., either the presence or absence of a cardiac arrhythmia and stores the diagnostic conclusion within a memory of external device 290 or another device. External device 290 may further output the determination of the presence of a cardiac arrhythmia as well as confirmation data supporting the same (552) or output the determination of the absence of a cardiac arrhythmia as well as confirmation data supporting the same (544). The output of the diagnostic conclusion may include storing such information in a non-transitory computer-readable memory and/or presenting an indication of the diagnostic conclusion to a user via a user interface.

Alternatively, upon determining the initial set of diagnostic data is insufficient to reach a diagnostic conclusion of the presence or absence of a cardiac arrhythmia according to the diagnostic algorithm, external device 290 requests additional data from IMD 205. In this example, the additional data represents additional information for the cardiac events of the initial iteration, including one EKG channel/vector at eight-bit resolution and 200 samples per second for cardiac episodes including heartrates of at least 160 BPM (512). In response to the request, IMD 205 transmits an additional set of diagnostic data to external device 290, the additional set of diagnostic data including the requested data (514). The volume of data within this iteration of diagnostic data may range between 1 and 10 megabytes, such as approximately 3 megabytes, such that data transfer between IMD 205 and external device 290 under any variety of wireless connections is still practical, although more time and power may is required than with the initial data transfer of step 504.

External device 290 receives the additional diagnostic data from IMD 205, and analyzes, via a diagnostic algorithm, such as arrhythmia detection module 130, the additional diagnostic data in combination with the initial set of diagnostic data to determine the presence or absence of a cardiac arrhythmia (516). In the event that diagnostic data is sufficient to declare a disease state, external device 290 declares the diagnostic conclusion as discussed above with respect to the initial iteration. In the event the combined diagnostic data is insufficient to reach a diagnostic conclusion according to the diagnostic algorithm, external device 290 may again request additional data from IMD 205. In this example, the additional data represents additional information for the cardiac events of the prior iterations, including one EKG channel/vector at sixteen-bit resolution and 500 samples per second for cardiac episodes including heartrates of at least 160 BPM (522). In response to the request, IMD 205 transmits an additional set of diagnostic data to external device 290, the additional set of diagnostic data including the requested data and optionally including onset EKG data, such as thirty seconds of onset EKG data, for each of the cardiac episodes (524). The volume of data within this iteration of diagnostic data may range between 10 and 100 megabytes, such as approximately 50 megabytes, such that data transfer between IMD 205 and external device 290 under any variety of wireless connections may still be practical, although more time and power is required than with prior iterations.

External device 290 receives the additional diagnostic data from IMD 205, and analyzes, via a diagnostic algorithm, such as arrhythmia detection module 130, the additional diagnostic data in combination with the diagnostic data of the prior iterations to determine the presence or absence of a cardiac arrhythmia (526). In the event that the diagnostic data is sufficient to declare a disease state, external device 290 declares the diagnostic conclusion as discussed above with respect to the initial iteration. In the event the combined diagnostic data is insufficient to reach a diagnostic conclusion according to the diagnostic algorithm, external device 290 may again request additional data from IMD 205. In this example, the additional data represents a complete EKG record recorded by IMD 105 (e.g., prior 180 days) at full fidelity including the maximum resolution and samples per second (532). The storage of a continuous EKG within a memory of IMD 205 is facilitated by the higher data storage capacities provided by the rapid improvements in semiconductor technologies.

In response to the request, IMD 205 transmits an additional set of diagnostic data to external device 290, the additional set of diagnostic data including the requested data EKG data at full fidelity (534). The volume of data within this iteration of diagnostic data may range between 1 and 100 gigabytes, such as approximately 50 gigabytes, such that data transfer between IMD 205 and external device 290 under some wireless connections may be impractical. For this reason, a higher speed or lower power wireless connection between IMD 205 and external device 290 may be used than with prior iterations. Examples of relatively suitable wireless connections for large volumes of data include inductive telemetry and externally powered communications like RFID. In some examples, external device 290 may notify a user via user interface 254 that an antenna of external device needs to be positioned in closer proximity to IMD 205 or an antenna of IMD 205 to facilitate the data transfer. In such examples, external device 290 and IMD 205 may communicate via a more convenient wireless connection, such as an RF connection, for example a Bluetooth or MICS connection, in prior iterations before switching to lower power, but less convenient, communication technique for the data transfer iteration of step 534.

External device 290 receives the additional diagnostic data from IMD 205, and analyzes, via a diagnostic algorithm, such as arrhythmia detection module 130, the additional diagnostic data in combination with the diagnostic data of the prior iterations to determine the presence or absence of a cardiac arrhythmia (536). In the event that the diagnostic data is sufficient to declare a disease state, external device 290 declares the diagnostic conclusion as discussed above with respect to the initial iteration. In the event the diagnostic data is insufficient to reach a diagnostic conclusion according to the diagnostic algorithm, external device 290 declares the diagnostic data is insufficient to reach a diagnostic conclusion (546). External device 290 may store an indication that the diagnostic data is insufficient to reach a diagnostic conclusion within a memory of external device 290 or another device and/or present an indication that the diagnostic data is insufficient to reach a diagnostic conclusion to a user via user interface 254.

Various techniques of this disclosure, including techniques described with respect to diagnostic algorithms, IMD 105, external device 190 including arrhythmia detection module 130, IMD 205 including implant control circuit 236, and external device 290 including arrhythmia detection module 130 may be implanted in hardware, software or any suitable combination thereof. Such hardware includes, but is not limited to, one or more processors or microprocessors, digital signal processors (DSP), application specific integrated circuits (ASIC), processors with firmware, field programmable gate arrays (FPGA), or any other combination of hardware on a single device or distributed across multiple devices including more than one IMD and/or more than one external device.

In addition to the embodiments described for a medical diagnosis aspects of the subject matter disclosed herein also can be used for progressive and adaptive data transfer for device or system diagnosis. In an embodiment progressive and adaptive transfer data is used to diagnose a potential failure in an implantable or wearable device. Examples of potential failures include a memory failure, a sensor failure, a power source failure, a processor failure, a passive component (e.g. capacitor) failure, a security failure, a hardware failure, a software failure and a firmware failure.

According to embodiments, aspects of embodiments of the techniques, processes, and methods described herein may be implemented in any number of different system contexts. For example, embodiments of the methods described with regard to FIGS. 3, 4, and 5 may be implemented in any number of different combinations of types of devices. That is, for instance, embodiments of the methods may be utilized for adaptively transferring data from one or more medical devices (IMDs, EMDs, etc.) to one or more other medical devices (IMDs, EMDs, etc.), one or more user devices (e.g., laptops, cell phones, programmers, etc.), one or more servers, and/or the like. Thus, although the embodiments described above with respect to FIGS. 1-5 are described in the context of IMDs communicating with devices outside of a patient's body, any number of aspects of those embodiments may be implemented using medical devices outside of the patient's body instead of, or in addition to, IMDs.

Additionally, an external device may communicate with a medical device directly and/or via one or more other devices. For example, in embodiments, a server or other device may be configured to perform an analysis (e.g., the diagnostic algorithm) and, upon determining that more data is to be acquired for the algorithm, the server may request that data from an external device (e.g., a cell phone or other mobile device, programmer, EMD, etc.). The external device may determine whether it has the requested data, provide the requested data to the server if so, and, if not, may request the data from the medical device. Similarly, components of a diagnostic algorithm or algorithms may be instantiated on multiple external devices, medical devices, and/or the like.

Accordingly, "medical device" may refer to any type of implantable medical device (IMD), external monitoring device (EMD), and/or the like; and "external device" may refer to any device other than the medical device (that is, e.g., any device that is external to the medical device). In embodiments, an IMD and/or an EMD may provide one or more of the following functions with respect to a patient: sensing, data analysis, and therapy. For example, in embodiments, an IMD and/or an EMD may be used to measure any number of a variety of physiological, device, subjective, and/or environmental parameters associated with a subject, using electrical, mechanical, and/or chemical means. The IMD and/or the EMD may be configured to automatically gather data, gather data upon request (e.g., input provided by the subject, a clinician, another device, and/or the like), and/or any number of various combinations and/or modifications thereof. The IMD and/or EMD may be configured to store data related to the physiological, device, environmental, and/or subjective parameters and/or transmit the data to any number of other devices. In embodiments, the IMD and/or the EMD may be configured to analyze data and/or act upon the analyzed data. For example, the IMD and/or EMD may be configured to modify therapy, perform additional monitoring, and/or provide alarm indications based on the analysis of the data.

According to embodiments, an IMD may include any type of IMD, any number of different components of an implantable system, and/or the like. For example, an IMD may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject and/or the IMD. In various embodiments, the IMD may include both defibrillation and pacing/CRT capabilities (e.g., a CRT-D device). The IMD may be implanted subcutaneously within an implantation location or pocket in the patient's chest or abdomen and may be configured to monitor (e.g., sense and/or record) physiological parameters associated with the patient's heart. In embodiments, the IMD may be an implantable cardiac monitor (ICM) (e.g., an implantable diagnostic monitor (IDM), an implantable loop recorder (ILR), etc.) configured to record physiological parameters such as, for example, one or more cardiac electrical signals, heart sounds, heart rate, blood pressure measurements, oxygen saturations, and/or the like. In embodiments, the IMD may be configured to sense intrathoracic impedance, from which various respiratory parameters may be derived, including, for example, respiratory tidal volume and minute ventilation. Sensors and associated circuitry may be incorporated in connection with the IMD for detecting one or more body movement or body posture and/or position related signals. For example, accelerometers and/or GPS devices may be employed to detect patient activity, patient location, body orientation, and/or torso position. In embodiments, the IMD may be configured to monitor physiological parameters that may include one or more signals indicative of a patient's physical activity level and/or metabolic level, such as an acceleration signal. The IMD may be configured to sense and/or record at regular intervals, continuously, and/or in response to a detected event.

Derived parameters may also be monitored using the IMD and/or EMD. For example, a sleep sensor may rely on measurements taken by an implanted accelerometer that measures body activity levels. The sleep sensor may estimate sleeping patterns based on the measured activity levels. Other derived parameters include, but are not limited to, a functional capacity indicator, autonomic tone indicator, sleep quality indicator, cough indicator, anxiety indicator, and a cardiovascular wellness indicator for calculating a quality of life indicator quantifying a subject's overall health and well-being.

In various embodiments, the EMD may be a device that is configured to be portable with the subject, e.g., by being integrated into a vest, belt, harness, sticker; placed into a pocket, a purse, or a backpack; carried in the subject's hand; and/or the like, or otherwise operatively (and/or physically) coupled to the subject. The EMD may be configured to monitor (e.g., sense and/or record) physiological parameters associated with the subject and/or provide therapy to the subject. For example, the EMD may be, or include, a wearable cardiac defibrillator (WCD) such as a vest that includes one or more defibrillation electrodes. In embodiments, the EMD may include any number of different therapy components such as, for example, a defibrillation component, a drug delivery component, a neurostimulation component, a neuromodulation component, a temperature regulation component, and/or the like. In embodiments, the EMD may include limited functionality, e.g., defibrillation shock delivery and communication capabilities, with arrhythmia detection, classification and/or therapy command/control being performed by a separate device such as, for example, the IMD.

In embodiments, the EMD may include sensing components such as, for example, one or more surface electrodes configured to obtain an electrocardiogram (ECG), one or more accelerometers configured to detect motion associated with the patient, one or more respiratory sensors configured to obtain respiration information, one or more environmental sensors configured to obtain information about the external environment (e.g., temperature, air quality, humidity, carbon monoxide level, oxygen level, barometric pressure, light intensity, sound, and/or the like) surrounding the patient, and/or the like. In embodiments, the EMD may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like. According to embodiments, the EMD may be configured to measure subjective and/or perceptive data from the subject.

Various modifications and additions can be made to the examples discussed without departing from the scope of the present disclosure. For example, while the examples described above refer to particular features, the scope of this this disclosure also includes examples having different combinations of features and examples that do not include all of the described features. Accordingly, the scope of the present this disclosure is intended to embrace all such alternatives, modifications, and variations as fall within the scope of the claims, together with all equivalents thereof.

What is claimed is:

1. An interrogation system for a medical device comprising:
    a memory storing a diagnostic algorithm;
    a processor configured to run the diagnostic algorithm; and
    a communication module configured to facilitate data transfer between the interrogation system and the medical device,
    wherein the diagnostic algorithm is configured to reach a diagnostic conclusion based on data from the medical device,
    wherein the diagnostic algorithm is configured to iteratively interrogate the medical device for the data from the medical device until the diagnostic algorithm reaches the diagnostic conclusion corresponding to an arrhythmia state of a subject associated with the medical device, wherein the arrhythmia state corresponds to the subject having a presence or an absence of a cardiac arrhythmia, each iterative interrogation requesting additional data as compared to prior iterations, wherein the diagnostic algorithm interrogates the medical device more than once to request additional data as compared to prior iterations before the diagnostic algorithm reaches the diagnostic conclusion corresponding to the arrhythmia state wherein the diagnostic algorithm reaches the diagnostic conclusion corresponding to the arrhythmia state based on the requested additional data, and wherein the diagnostic algorithm ceases to request the additional data either (i) once the diagnostic algorithm reaches the diagnostic conclusion or (ii) all of the data corresponding to diagnostic data stored by the medical device has been transferred from the medical device to the interrogation system,
    wherein the communication module is configured to receive the additional data from the medical device in response to each iterative interrogation, and
    wherein the diagnostic algorithm is further configured to store an indication of the diagnostic conclusion within the memory.

2. The interrogation system of claim 1, wherein the processor is configured to select a communication technique for the data transfer between the interrogation system and the medical device according to at least one of a volume of the data in the data transfer, a time available for the data transfer, and an energy available for the data transfer.

3. The interrogation system of claim 2, wherein the selected communication technique includes one or more of:
    radio frequency communications;
    inductive communications; and
    externally powered communications.

4. The interrogation system of claim 1, wherein the diagnostic algorithm is configured to detect atrial fibrillation.

5. The interrogation system of claim 1, wherein the additional data includes an additional data type as compared to prior iterations.

6. The interrogation system of claim 1, wherein the additional data includes data representing additional events as compared to prior iterations.

7. The interrogation system of claim 1, wherein the additional data includes one or more of:
    a higher data sample rate as compared to prior iterations;

a higher data sample resolution as compared to prior iterations;
a longer data sample length as compared to prior iterations; and
a lower data sample threshold as compared to prior iterations.

8. The interrogation system of claim 1, wherein the memory, the processor and the communication module are part of a clinician programmer.

9. A medical system comprising:
a medical device comprising a housing encasing control electronics, a medical device communication module, and a medical device memory, wherein the control electronics are configured to store diagnostic data within the memory; and
an interrogation system for a medical device comprising:
a memory storing a diagnostic algorithm;
a processor configured to run the diagnostic algorithm; and
a communication module configured to facilitate data transfer between the interrogation system and the medical device,
wherein the diagnostic algorithm is configured to iteratively interrogate the medical device for the data from the medical device until the diagnostic algorithm reaches a diagnostic conclusion corresponding to an arrhythmia state of a subject associated with the medical device, wherein the arrhythmia state corresponds to a presence or an absence of a cardiac arrhythmia, each iterative interrogation requesting additional data as compared to prior iterations, wherein the diagnostic algorithm interrogates the medical device more than once to request additional data as compared to prior iterations before the diagnostic algorithm reaches the diagnostic conclusion corresponding to the arrhythmia state, wherein the diagnostic algorithm reaches the diagnostic conclusion corresponding to the arrhythmia state based on the requested additional data, and wherein the diagnostic algorithm ceases to request the additional data either (i) once the diagnostic algorithm reaches the diagnostic conclusion or (ii) all of the data corresponding to diagnostic data stored by the medical device has been transferred from the medical device to the interrogation system,
wherein the control electronics are configured to provide requested portions of the diagnostic data to the interrogation system via the medical device communication module in response to the iterative interrogations from the communication module of the interrogation system,
wherein the communication module is configured to receive the additional data from the medical device in response to each iterative interrogation,
wherein the diagnostic algorithm is configured to reach the diagnostic conclusion based on data from the medical device, and
wherein the diagnostic algorithm is further configured to store an indication of the diagnostic conclusion within the memory.

10. The medical system of claim 9, wherein the processor is configured to select a communication technique for the data transfer between the interrogation system and the medical device according to at least one of a volume of the data in the data transfer, a time available for the data transfer, and an energy available for the data transfer.

11. The medical system of claim 10, wherein the selected communication technique includes one or more of:
radio frequency communications;
inductive communications; and
externally powered communications.

12. The medical system of claim 9, wherein the additional data includes one or more of:
an additional data type as compared to prior iterations;
data representing additional events as compared to prior iterations;
a higher data sample rate as compared to prior iterations;
a higher data sample resolution as compared to prior iterations;
a longer data sample length as compared to prior iterations; and
a lower data sample threshold as compared to prior iterations.

13. The medical system of claim 9, wherein the memory, the processor and the communication module are part of a clinician programmer.

14. The medical system of claim 9, wherein the medical device includes one or more of:
an electrical stimulation device;
a drug delivery device; and
a physiological sensor.

* * * * *